US006350922B1

(12) United States Patent
Vosejpka et al.

(10) Patent No.: US 6,350,922 B1
(45) Date of Patent: Feb. 26, 2002

(54) PROCESS FOR MAKING 2,3-DIHALOPROPANOLS

(75) Inventors: Paul C. Vosejpka; Dennis A. Hucul; Bob R. Maughon; Larry N. Ito; Robert M. Campbell, all of Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/464,682

(22) Filed: Dec. 16, 1999

Related U.S. Application Data

(60) Provisional application No. 60/112,839, filed on Dec. 18, 1998.

(51) Int. Cl.[7] ............................................... C07C 29/38
(52) U.S. Cl. ........................ 568/846; 568/841; 568/842
(58) Field of Search .................................. 568/841, 842, 568/846; 549/514, 520

(56) References Cited

U.S. PATENT DOCUMENTS

| | | |
|---|---|---|
| 2,860,146 A | 11/1958 | Furman et al. |
| 4,008,281 A | 2/1977 | Knowles et al. |
| 4,049,577 A | 9/1977 | Childress et al. |
| 4,129,600 A | 12/1978 | Childress et al. |
| 4,166,808 A | 9/1979 | Daumas et al. |
| 5,225,389 A | 7/1993 | Caillod et al. |
| 5,326,916 A | 7/1994 | Kobayashi et al. |
| 5,744,655 A | 4/1998 | Thomas et al. |
| 6,008,419 A | 12/1999 | Thomas et al. |

FOREIGN PATENT DOCUMENTS

| | | |
|---|---|---|
| AU | 630238 | 4/1991 |
| GB | 2175896 A | 12/1986 |

OTHER PUBLICATIONS

Rylander, *Catalytic Hydrogenation in Organic Syntheses*, Academic Press, 1979, Cover Page Only.
Rylander, *Catalytic Hydrogenation over Platinum Metals*, Academic Press, 1967, Cover Page Only.
Rylander, *Hydrogenation Methods*, Academic Press, 1985, Cover Page Only.
Preparation of Catalysts III, Scientific Bases for the Preparation of Heterogeneous Catalysts, Studies in Surface Science and Catalysis 16, Proceedings of the Third International Symposium, Louvain–la–Neuve, Sep. 6–9, 1982, Cover Page Only.
Kuwahara et al., "Hydrogenation of CO Over Silica–Supported Mo Ir Catalysts," *Chemistry Letters*, pp. 205–206, 1985.
van Gruijthuijsen et al., "Structure and Reactivity of Bimetallic FeIr/SiO$_2$ Catalysts after Reduction and during High –Pressure CO Hydrogenation," *J. of Catalysis*, 170, pp. 331–345, 1997.
Kintaichi et al., "Hydrogenation of Carbon Monoxide into C$_2$–Oxygenated Compounds over Silica–supported Bimetallic Catalyst Composed of Ir and Ru," *Sekiyu Gakkaishi*, 41, pp. 66–70, 1998.
Hamada, "Hydrogenolysis of n–Butane on Silica–Supported Ru–Ir Bimetallic Catalysts," *Applied Catalysis*, 27, pp. 265–273, 1986.

*Primary Examiner*—Jean F. Vollano

(57) ABSTRACT

A process for making 2,3-dihalopropanol including reacting 2,3-dihalopropanal with a hydrogenating agent in the presence of an iridium and a second transition metal mixed metal catalyst where the second transition metal is selected from the group comprising ruthenium, iron, molybdenum, tungsten, rhenium, osmium, manganese or vanadium, under conditions such that 2,3-dihalopropanol is formed. The 2,3-dihalopropanol is particularly useful in a process for making epihalohydrin.

27 Claims, No Drawings

PROCESS FOR MAKING 2,3-DIHALOPROPANOLS

This application claims the benefit of U.S. Provisional Application No. 60/112,839, filed Dec. 18, 1998.

BACKGROUND OF THE INVENTION

The present invention relates to a process for making 2,3-dihalopropanols utilizing an iridium metal plus a second transition metal mixed metal catalyst wherein the second transition metal comprises ruthenium, iron, molybdenum, tungsten, rhenium, osmium, manganese or vanadium.

Mixed transition metal catalysts have been made previously. For example, Hamada, et al., in Appl. Catal., 1986, 27, 265–73; and Sekiyu Gakkaishi 1998, 41, 66–70, incorporated herein by reference, report the preparation of iridium/ruthenium mixed metal heterogeneous catalysts for the hydrogenation of carbon monoxide and the hydrogenolysis of n-butane; Van Gruijthuijsen, et al., in J. Catal., 1997, 170, 331–345, incorporated herein by reference, report the preparation of iridium/iron mixed metal heterogeneous catalysts for the hydrogenation of carbon monoxide; and Kuwahara, et al., in Chemistry Letters, 1985, 205–206, incorporated herein by reference, report the preparation of iridium/molybdenum mixed metal heterogeneous catalysts for the hydrogenation of carbon monoxide.

U.S. Pat. No. 5,744,655 issued to Thomas et al., Apr. 28, 1998, discloses a process for making a 2,3-dihalopropanol by reacting 2,3-dihalopropanal with a hydrogenating agent in the presence of a transition metal-containing catalyst, under conditions such that 2,3-dihalopropanol is formed.

Several catalysts for the above reduction reaction of 2,3-dihalopropanol are disclosed in U.S. Pat. No. 5,744,655 and in U.S. patent application Ser. No. 994,208, entitled "Process For Making 2,3-Dihalopropanols" filed Dec. 19, 1997, by Thomas et al. including catalysts containing a "Group VIIIA metal selected from iron, cobalt, nickel, ruthenium, rhodium, palladium, osmium, iridium, platinum and mixtures thereof." The catalysts known in the prior art are selected to provide high conversion and selectivity in single batch-type reactions. No real emphasis is placed on catalysts with sustained conversion and selectivity.

It is desired therefore to provide a hydrogenation process for converting 2,3-dihalopropanal to 2,3-dihalopropanol using a transition metal catalyst wherein the catalyst provides sustained hydrogenation activity at high conversion and selectivity.

SUMMARY OF THE INVENTION

One aspect of the present invention is directed to the discovery of mixtures of an iridium metal, as a first transition metal, and a second transition metal selected from the group comprising ruthenium, iron, molybdenum, tungsten, rhenium, osmium, manganese or vanadium metal on a support useful as catalysts for the hydrogenation of 2,3-dihalopropanal to 2,3-dihalopropanol. The iridium metal plus the second transition metal used as a mixed metal catalyst efficiently converts 2,3-dihalopropanal with high selectivity to 2,3-dihalopropanol and also exhibits unexpected sustained activity for the hydrogenation reaction. No one prior to the inventors of the present invention has used an iridium/second transition metal mixture as a catalyst for the hydrogenation of 2,3-dihalopropanal to 2,3-dihalopropanol.

Another aspect of the present invention is a process to make 2,3-dihalopropanol using the above catalysts comprising the step of reacting 2,3-dihalopropanal with a hydrogenating agent in the presence of the above iridium/second transition metal mixed metal catalysts, under conditions such that 2,3-dihalopropanol is formed.

Yet another aspect of the present invention is a process to make epihalohydrin comprising the steps of:
(1) reducing 2,3-dihalopropanal to form 2,3-dihalopropanol as described above; and
(2) cyclizing 2,3-dihalopropanol to make epihalohydrin.

This process for producing epihalohydrin advantageously uses only about one mole of molecular halogen per mole of epihalohydrin produced. This process reduces the amount of halogenated organics in the waste stream by more than 60 percent, relative to the commercial allyl chloride route. This process also uses substantially less water than the allyl chloride route. The reducing agent may be hydrogen, so that there is no need to recycle ketone to alcohol, as in transfer hydrogenation.

DETAILED DESCRIPTION OF THE INVENTION

The process of the present invention for making 2,3-dihalopropanol from a 2,3-dihalopropanal, generally, is a reduction reaction of an aldehyde to an alcohol. The reduction is carried out by hydrogenating a dihalopropanal to a dihalopropanol in the presence of a catalyst.

The catalysts useful in the present invention are selected such that under reaction conditions they catalyze the hydrogenation of substantially all of the aldehyde moieties on the dihalopropanal molecule to primary alcohol moieties without substantially affecting the halogens which are bonded to the molecule. The catalyst is advantageously a combination of iridium metal with a second transition metal comprising ruthenium, iron, molybdenum, tungsten, rhenium, osmium, manganese or vanadium in an effective ratio to provide a sustained high catalytic activity and a high selectivity to the dihalopropanol.

As an illustration of the present invention, for example, for iridium/ruthenium mixed metal catalysts the atomic ratio of iridium metal to ruthenium metal in the catalyst is generally from about 0.02 to about 15, preferably from about 0.05 to about 10, more preferably from about 0.15 to about 8, and most preferably from about 0.3 to about 2.0.

The selectivity for 2,3-dihalopropanol formation using the iridium/ruthenium mixed metal catalysts is greater than about 75%, preferably greater than 80% and more preferably greater than 90%.

The catalyst useful in the present invention also preferably has an initial catalyst activity in batch reactions of greater than about 50% dihalopropanal conversion at 30 minutes for a first charge of 2.5 grams dihalopropanal/gram catalyst and a second measured catalyst activity using the same catalyst of at least greater than about 50% dihalopropanal conversion at 30 minutes for a second charge of 2.5 grams dihalopropanal/gram catalyst. Although these are the preferred initial catalyst activities for a first charge of 2.5 grams dihalopropanal/gram catalyst, the catalyst can certainly be reacted with charges of less than 2.5 grams dihalopropanal/gram catalyst.

The catalyst useful in the present invention may be in homogeneous or heterogeneous form. Preferably, the catalyst is a heterogeneous catalyst.

The heterogeneous catalysts useful in the present invention may be, for example, an iridium metal and a second transition metal deposited or absorbed on an insoluble support such as silica, silylated silica, carbon, alumina, zirconia, titania, magnesia, and other common supports known in the art. Supports which can be used in the present invention are described in Poncelet et al. editors, *Preparation of Catalysts III*, New York, 1983; P. N. Rylander, *Hydrogenation Methods*, Academic Press, London, 1985; P. N. Rylander, *Catalytic Hydrogenation Over Platinum Metals*, Academic Press, New York, 1967; P. Rylander, *Catalytic Hydrogenation in Organic Syntheses*, Academic Press, New York, 1979, incorporated herein by reference. Also, the heterogeneous catalyst useful in the present invention may be an iridium metal and a second transition metal coordinated to ligands bonded to a resin, for example, on phosphinated polystyrene. The total weight percent of metal loading on the support is preferably from 0.001 to about 50 weight percent, more preferably from 0.01 to about 10 weight percent; and most preferably 0.05 to about 5 weight percent.

The homogeneous catalyst useful in the reaction mixture of the present invention contains mixtures of soluble iridium and second transition metal compounds or a soluble iridium/second transition metal mixed metal complex. Examples of soluble metal compounds include halides, acetoacetates, acetates and hydroxides of iridium and the second transition metal. A homogeneous catalyst useful in the present invention includes, for example, a $RuCl_3$ and $IrCl_3$ mixture.

The homogeneous catalysts useful in the present invention may further contain a coordinating ligand. Examples of suitable coordinating ligands include for example phosphines, 1,5-cyclooctadiene (COD), norbornadiene (NBD), arsines, stibines, carbon monoxide, ethers, cyclopentadienyl (Cp), aromatic amines, sulfoxides such as dimethyl sulfoxide (DMSO) and mixtures thereof. Examples of suitable phosphines include, in particular, triaryl phosphine and more particularly triphenyl phosphine. A specific example of a homogeneous catalyst useful in the present invention includes a mixture of $RuCl_2$ $(PPh_3)_3$ and (COD)$Ir(PPh_2Me)_2{}^+PF_6{}^-$.

The homogeneous catalyst useful in the reaction mixture of the present invention may also consist of a mixture of a soluble iridium and second transition metal compounds or complexes with added coordinating ligand such as for example $RuCl_3$ and $IrCl_3$ with $PPh_3$.

The iridium/second transition metal mixed metal catalysts of the present invention as described above are advantageously used in a hydrogenation reaction to form 2,3-dihalopropanols from 2,3-dihalopropanals. 2,3-Dihalopropanols are important intermediates in the manufacture of epihalohydrin.

The 2,3-dihalopropanols of the present invention are generally represented by the following:

Formula I

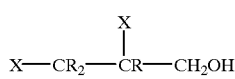

wherein each "X" is independently a halogen, is preferably chlorine or bromine and is most preferably chlorine; and each "R" is independently hydrogen or a lower ($C_1$ to $C_6$) hydrocarbyl group, is preferably hydrogen or a lower alkyl group, is more preferably hydrogen or a methyl group and is most preferably hydrogen. 2,3-Dichloropropanol is the most commonly used member of the class.

The 2,3-dihalopropanals of the present invention are generally represented by the following:

Formula II

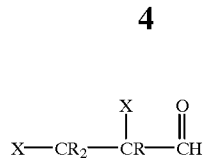

wherein each "X" is independently a halogen, is preferably chlorine or bromine and is most preferably chlorine; and each "R" is independently hydrogen or a lower ($C_1$ to $C_6$) hydrocarbyl group, is preferably hydrogen or a lower alkyl group, is more preferably hydrogen or a methyl group and is most preferably hydrogen.

Examples of suitable 2,3-dihalopropanals useful in the present invention include: 2,3-dichloropropanal; 2,3-dibromopropanal; 2,3-dichloro-2-methylpropanal, 2,3-dibromo-2-methylpropanal and mixtures thereof. The 2,3-dihalopropanal used in the present invention is most preferably an unsubstituted 2,3-dichloropropanal to form 2,3-dichloropropanol. An unsubstituted 2,3-dibromopropanal can also be used to form 2,3-dibromopropanol.

The dihalopropanal is hydrogenated by reacting the dihalopropanal with a hydrogenating agent in the presence of the catalyst of the present invention. The hydrogenation reaction is described in detail in U.S. Pat. No. 5,744,655, incorporated herein by reference. The hydrogenating agent useful in the present invention may be, for example, molecular hydrogen, alcohols, hydrazines, formates or combinations thereof. Examples of suitable alcohols useful as the hydrogenating agent in the present invention can be primary or secondary alcohols such as methanol, ethanol and $C_3$ to $C_{10}$ primary and secondary alcohols. Examples of other secondary alcohols useful in the present invention are described in U.S. Pat. No. 2,860,146, incorporated herein by reference. The hydrogenating agent used in the present invention is preferably molecular hydrogen.

The hydrogenation reaction consumes one mole of hydrogenating agent per mole of dihalopropanol which is made. Generally, at least about 0.6 moles of hydrogenating agent per mole of 2,3-dihalopropanal are available to be consumed during the course of the reaction, preferably at least about 0.75 moles of molecular hydrogen per mole of 2,3-dihalopropanal are available to be consumed during the course of the reaction, more preferably at least about 0.9 moles and most preferably at least about 1 mole are available to be consumed during the course of the reaction. When less than 1 mole of hydrogenating agent per mole of 2,3-dihalopropanal is available to be consumed during the course of the reaction, the reaction is less efficient because complete conversion of the 2,3-dihalopropanal is not obtained. However, not all of the hydrogenating agent need be available at the start of the reaction. The hydrogenating agent may be added step-wise or continuously as the reaction progresses. In this case, the reaction mixture at any one time may contain a stoichiometric excess of dihalopropanal over hydrogenating agent. As one embodiment of the present invention, an excess of hydrogenating agent required may be used for completing the conversion in the reaction. Generally, for example, from 10 percent to 20 percent excess hydrogenating agent may be used.

The maximum quantity of hydrogenating agent source is not critical and is governed by practical considerations such as pressure, reactor efficiency and safety. When the hydrogenating agent source is gaseous, then the quantity of hydrogenating agent is preferably at least enough to provide the desired pressure. However, in most cases, the reactor preferably contains no more than about 1,000 moles of molecular hydrogen per mole of 2,3-dihalopropanal and more preferably contains no more than about 100 moles. Gaseous hydrogenating agent sources, such as molecular hydrogen, are preferably used according to known methods for mixing a gaseous reagent with a liquid reaction mixture, such as bubbling the gas through the mixture with agitation or solubilizing the hydrogen under pressure.

The hydrogenation reaction is optionally, but preferably carried out in the presence of a solvent. The solvent may be protic, aprotic or mixtures thereof. The solvent is preferably inert with respect to all of the reagents under the reaction conditions. The solvent may be selected such that: (1) the solvent does not boil under reaction conditions; and (2) 2,3-dihalopropanol can be recovered from the solvent by distillation or extraction. Examples of solvents useful in the present invention include water, carboxylic acids, phenolic compounds, aliphatic alcohols, aromatic and aliphatic hydrocarbons, carbonates, ethers, glymes, glycol ethers, halogenated hydrocarbons and mixtures thereof. Specific examples of the solvents useful in the present invention include water, acetic acid, phenol, methanol, 2,3-dichloropropanol, toluene, cyclohexane, hexane, propylene carbonate, dioxane, diphenyl ether, diglyme, 1,2-dimethoxyethane, methylene chloride, ethylene dichloride and mixtures thereof.

The quantity of solvent is not critical and is governed primarily by practical considerations, such as the ability to dissolve the catalyst (in the case of homogeneous catalysts) and the efficiency of the reactor.

Generally, the amount of solvent which can be present in the reaction mixture of the present invention is from 0 to about 99.99 weight percent, preferably from 0 to about 95 weight percent; and more preferably 0 to about 90 weight percent; most preferably 0 to 80 percent.

In most cases, the hydrogenation reaction mixture preferably contains at least about 5 weight percent 2,3-dihalopropanal, more preferably at least about 10 weight percent and most preferably at least about 20 weight percent. The reaction can also be run neat in 2,3-dihalopropanal (about 100 weight percent 2,3-dihalopropanal).

The reaction mixture frequently contains minor quantities of strong mineral acids such as hydrogen halide, which may cause certain side reactions. The reaction may be carried out in the presence of an acid scavenger. Examples of suitable acid scavengers useful in the present invention include alkali metal carbonates; alkali metal bicarbonates; quaternary ammonium or phosphonium carboxylates, bicarbonates, carbonates; alkali metal carboxylates; epoxides and mixtures thereof. Specific examples of acid scavengers include sodium carbonate, sodium bicarbonate, ethylene oxide, propylene oxide, butylene oxide, epichlorohydrin and mixtures thereof. Epichlorohydrin is the preferred epoxide to serve as an acid scavenger. Generally, the molar ratio of acid scavenger to 2,3-dihalopropanal in the reaction mixture is from about 0.01 to about 1, and preferably from about 0.01 to about 0.5 and most preferably from about 0.01 to about 0.1.

The temperature of the hydrogenation reaction is not critical, provided that all of the reagents and catalyst are in intimate contact with each other. However, low temperatures require longer reaction times. The reaction temperature is preferably at least about −10° C., more preferably at least about 20° C. and most preferably at least about 50° C. The reaction temperature is preferably less than about 250° C., more preferably no more than about 150° C. and most preferably no more than about 120° C. The reaction temperature is preferably from about 0° C. to about 200° C. and more preferably from about 50° C. to about 120° C.

The hydrogenation reaction pressure is not critical as long as there is sufficient hydrogen in the reaction mixture to run the reaction. The pressure is preferably at least about 14 psia (97 kPa, 1 atmosphere) and more preferably at least about 50 psia (340 kPa, 3.4 atmospheres). The pressure is preferably no more than about 3,000 psia (21 MPa, 220 atmospheres). Higher pressures could lead to shorter reaction times.

The product of the hydrogenation reaction is a 2,3-dihalopropanol with a structure derived from the 2,3-dihalopropanal. The product may be recovered by known methods, such as extraction or distillation. The product may be recovered in yields as low as 2 percent, however, for economical purposes the product of the present invention is generally recovered in at least about 60 percent yields (based upon the initial quantity of 2,3-dihalopropanal), and preferably recovered in at least about 80 percent yields, more preferably in at least about 90 percent yields and most preferably in at least about 95 percent yields.

The hydrogenation reaction is particularly useful in a process for making epichlorohydrin. Once the 2,3-dihalopropanol is made using the reaction of the present invention, the 2,3-dihalopropanol may be cyclized to make epihalohydrin by processes well-known in the art. More particularly, the catalyzed hydrogenation reaction step of the present invention may be used in a four-step process to make epichlorohydrin from propylene as follows:

In Step (1), a 3-carbon hydrocarbon such as propylene is oxidized to form acrolein. Processes for this reaction are already well-known in the art and are described in the following references, which are incorporated herein by reference: Watanabe et al. (U.S. Pat. No. 4,008,281 (Feb. 15, 1977)); Childress et al. (U.S. Pat. No. 4,049,577 (Sep. 20, 1977)); Childress et al. (U.S. Pat. No. 4,129,600 (Dec. 12, 1978)); Daumas et al. (U.S. Pat. No. 4,166,808 (Sep. 4, 1979)); Caillod et al. (U.S. Pat. No. 5,225,389 (Jul. 6, 1993)) and Kobayashi et al. (U.S. Pat. No. 5,326,916 (Jul. 5, 1994)). In most cases, propylene is contacted in a gaseous phase with oxygen in the presence of a catalyst such as bismuth-phosphorous-molybdenum. Acrolein can also be made by oxidation of allyl alcohol. Acrolein is also commercially available, for example, from Aldrich Chemical Company, Inc. and Fisher Scientific Acros Organics.

In Step (2), acrolein is halogenated to make 2,3-dihalopropanal. This step has been described in U.S. Pat. No. 2,860,146, which is incorporated herein by reference. Preferably, the acrolein is contacted with molecular halogen, which is preferably molecular chlorine or molecular bromine and is more preferably molecular chlorine. The reaction temperature of Step (2) is preferably no more than about 125° C. and more preferably no more than about 50° C. It is preferably at least about −10° C. and more preferably at least about 0° C. The reaction of Step (2) can be run neat, or can take place in the presence of an organic solvent which is substantially inert with respect to all reagents under reaction conditions. Examples of suitable solvents useful in Step (2) include halogenated hydrocarbons, such as methylene chloride, 1,2-dichloroethane and 1,2-dichloropropane; dioxane; aliphatic hydrocarbons such as pentane, hexane, heptane; and mixtures thereof.

The concentration of water in the reaction mixture of Step (2) is preferably minimized because water can react with the 2,3-dihalopropanal product to form impurities.

The halogen, for example chlorine, partial pressure is preferably at a value which is balanced by the reactor heat removal rate. For example, the halogen partial pressure may be from about 0 (0 kPa) to about 30 psia (207 kPa). The yield of 2,3-dihalopropanal is preferably at least about 90 percent.

Step (3) is the reduction of 2,3-dihalopropanal to 2,3-dihalopropanol. The preferred embodiments of this step have been described previously in this application.

For example, one embodiment of the process of the present invention comprises the step of contacting a 2,3-dihalopropanal with at least a stoichiometric quantity of molecular hydrogen in the presence of a iridium/second transition metal mixed metal catalyst and a protic or an aprotic solvent or mixtures thereof and, optionally, wherein the mixture further contains an acid scavenger.

Step (4) is the conversion of 2,3-dihalopropanol to epihalohydrin. This step is well-known in the art of manufacturing epihalohydrin. The reaction of Step (4) is usually carried out by contacting the dihalopropanol with a strong base, such as an aqueous alkali metal hydroxide, including for example sodium hydroxide. Examples of the Step (4) reaction are described in U.S. Pat. No. 2,860,146 and Wernli et al. (Australian Patent 630,238 (Feb. 12, 1993)), which are incorporated herein by reference.

Processes, which use the present invention, may contain any one or more of Steps (1), (2) and (4), in addition to Step (3). They preferably contain Steps (2) and (3), more preferably contain Steps (2), (3) and (4) and most preferably contain Steps (1)–(4).

The following examples are for illustrative purposes only and should not be taken as limiting the scope of either the Specification or the Claims. Unless otherwise stated, all parts and percentages are by weight.

EXAMPLES 1–3 AND COMPARATIVE EXAMPLES A AND B

General Procedure

Heterogeneous catalysts were prepared by impregnation of silica (Davison 57) with aqueous metal salt solutions of $IrCl_3 \cdot 3H_2O$ and one of the following: $RuCl_3 \cdot H_2O$, $(NH_4)_6Mo_7O_{24} \cdot 4H_2O$, $MnCl_2 \cdot 4H_2O$, $OsCl_3 \cdot 3H_2O$, or $FeCl_3 \cdot 6H_2O$, or by impregnation of silica with ethanol solutions of $IrCl_3 \cdot 3H_2O$ and one of the following: $WCl_6$, $MoCl_5$, $VOCl_3$, or $ReCl_3$. The mixed metal systems could be prepared by co-impregnation or by impregnation of one metal salt (and dried) followed by the other. The catalysts were air dried and then prereduced under dynamic $H_2/N_2$ (5% hydrogen) at 200° C. The catalysts were then stored and handled in an inert atmosphere glove box.

A 300-mL Parr reactor vessel was loaded with a catalyst charge and the reactor vessel was evacuated and nitrogen flushed three times. A solvent/2,3-dichloropropanal (DCP) mixture was sparge degassed with nitrogen and added to the Parr reactor with a syringe. The reactor was pressurized/vented to 250/20 psig (1.7 mPa/138 kPa) nitrogen and 1000/20 psig (6.9 mPa/138 kPa) hydrogen, then placed under 1000 psig (6.9 mPa) hydrogen and heated to 65° C. to 100° C. Samples were removed by syringe after venting the reactor to less than 15 psig (103 kPa).

Samples were analyzed by gas chromatography (GC) using a Hewlett Packard HP-5890 gas chromatograph equipped with a 25 m HP-5 Ultra 2 capillary column with split injection. Approximately 120 μL of the reaction mixture was dissolved in 5.0 mL of chloroform which contained a known amount of chlorobenzene as a GC standard (typically 0.05 weight percent). "Selectivity" is defined as the molar ratio of the amount of 2,3-dihalopropanol formed to the amount of 2,3-dihalopropanal consumed.

A comparison of activity and selectivity over two successive batch cycles for pure ruthenium/silica, pure iridium/silica, and selected ruthenium/iridium/silica catalysts is presented in Table 1 below. The ability of the ruthenium/iridium catalysts to provide sustained hydrogenation activity with high selectivity superior to either the pure ruthenium or pure iridium catalysts is demonstrated.

The pure iridium catalyst (Comparative Example B) has good initial activity (79.3% conversion in 30 minutes) with high selectivity (greater than 99%), but the conversion for the second charge (Run No. 2) is poor (7.9% conversion in 30 minutes; 90% loss of activity).

The pure ruthenium catalyst (Comparative Example A) shows stable performance over two cycles (Run #1 and Run No. 2) with 20% loss in activity, but the activity of the ruthenium catalyst is low (24.7% and 19.7% conversion in 30 minutes) respectively.

The combination of iridium and ruthenium metal in catalysts of the present invention (Examples 1, 2 and 3) provides in all cases very good selectivity (greater than 90%) to 2,3-dihalopropanols. In addition, catalysts of the present invention show activities which in all cases are better than that observed for pure ruthenium (at least greater than 47% versus 24.7% and 19.7%); and the loss of activity between cycles (Runs No. 1 and Runs No. 2) for the catalysts of the present invention are superior to the pure iridium catalyst (32%, 33%, 13% all less than 90%).

In addition, the loss of activity for the catalysts of the present invention are comparable to, and in Example 3, superior to that of the pure ruthenium catalyst (13%; less than 20%).

Table 1 also compares activity and selectivity over two successive batch cycles for other iridium/transition metal mixed metal catalysts. While product selectivity for all the iridium/transition metal mixed metal catalysts remained high, the initial activity (Run No. 1, conversion after 30 minutes) was in all cases higher than the pure ruthenium catalyst (69, 80, 34, 95, 83, 41 and 79 all greater than 24.7%). With the exception of the Ir/Mn (94%) catalyst, the loss of activity from Run No. 1 to Run No. 2 was less than that exhibited by the pure iridium catalyst (78, 15, 70, 69, 63 and 81 all less than 90% loss of activity).

Table 2 compares the activity and selectivity over two successive batch cycles for the 2% iridium/0.5% ruthenium mixed metal catalyst on different catalyst support materials. These examples illustrate that the catalyst support can have a significant impact on initial activity, selectivity, and the loss in catalyst activity over multiple batch cycles.

TABLE 1

| Example[a] | Run No. | Catalyst Composition | g DCP[b]/ g Catalyst | Temperature (° C.) | Time (minutes) | Conversion (%) | Δ % Loss of Activity | Selectivity (%) |
|---|---|---|---|---|---|---|---|---|
| Example 1 | 1 | 2.0% Ru/ 0.5% Ir/Silica | 2.52 | 85 | 30 | 68.9 | 32 | 92.3 |
| | 2 | " | 2.51 | 84 | 30 | 47.2 | | 90.8 |

TABLE 1-continued

| Example[a] | Run No. | Catalyst Composition | g DCP[b]/ g Catalyst | Temperature (° C.) | Time (minutes) | Conversion (%) | Δ % Loss of Activity | Selectivity (%) |
|---|---|---|---|---|---|---|---|---|
| Example 2 | 1 | 1.5% Ru/ 1.0% Ir/Silica | 2.50 | 86 | 30 | 85.6 | 33 | 97.8 |
|  | 2 | " | 2.49 | 84 | 30 | 57.2 |  | 94.2 |
| Example 3 | 1 | 0.5% Ru/ 2.0% Ir/Silica | 2.50 | 84 | 30 | 100 | 13 | 98.6 |
|  | 2 | " | 2.50 | 85 | 30 | 87.4 |  | 98.2 |
| Comparative Example A | 1 | 2.5% Ru/Silica | 2.49 | 85 | 30 | 24.7 | 20 | 90.9 |
|  | 2 | " | 2.50 | 85 | 30 | 19.7 |  | 90.6 |
| Comparative Example B | 1 | 2.5% Ir/Silica | 2.48 | 85 | 30 | 79.3 | 90 | |
|  | 2 | " | 2.50 | 86 | 30 | 7.9 |  | >99 |
| Example 4 | 1 | 2.0% Ir/ 0.5% Fe/Silica | 3.88 | 85 | 30 | 69 | 78 | 94 |
|  | 2 | " | 3.57 | 85 | 30 | 15 |  | 89 |
| Example 5 | 1 | 2.0% Ir/ 0.5% Mo/Silica | 4.36 | 85 | 30 | 80 | 15 | 98 |
|  | 2 | " | 4.10 | 85 | 60 | 68 |  | 98 |
| Example 6 | 1 | 2.0% Ir/ 0.5% W/Silica | 4.00 | 85 | 30 | 34 | 70 | 96 |
|  | 2 | " | 4.00 | 85 | 60 | 10 |  | 85 |
| Example 7 | 1 | 2.0% Ir/ 0.5% Re/Silica | 3.93 | 85 | 30 | 95 | 69 | 97 |
|  | 2 | " | 4.01 | 85 | 30 | 29 |  | 90 |
| Example 8 | 1 | 2.0% Ir/ 0.5% V/Silica | 4.11 | 85 | 30 | 83 | 63 | 97 |
|  | 2 | " | 4.19 | 85 | 30 | 31 |  | 91 |
| Example 9 | 1 | 2.0% Ir/0.5% Mn | 4.10 | 85 | 30 | 41.31 | 93.8 | 99 |
|  | 2 | " | 4.10 | 85 | 30 | 2.57 |  | >99 |
| Example 10 | 1 | 2.0% Ir/0.5% Os | 4.10 | 85 | 30 | 78.67 | 80.6 | >99 |
|  | 2 | " | 4.10 | 85 | 30 | 15.23 |  | >99 |

[a]Reactions were run in a 600 mL Hastalloy C Parr reactor in cyclohexane under about 1000 psig $H_2$.
[b]DCP = dichloropropanal.

TABLE 2

| Example[a] | Support | Run No. | g DCP/ g Catalyst | Time (minutes) | Temperature (° C.) | Conversion (%) | Selectivity (%) |
|---|---|---|---|---|---|---|---|
| 11 | Alumina[b] | 1 | 4.13 | 15 | 83 | 57.5 | 92.4 |
|  | " | 2 | 4.13 | 15 | 86 | 40.0 | 21.8 |
| 12 | Silica-Magnesia[c] | 1 | 4.13 | 15 | 83 | 18.6 | 93.7 |
|  | " | 2 | 4.13 | 15 | 85 | 4.4 | 95.7 |
| 13 | Titanated Silica[d] | 1 | 4.13 | 15 | 84 | 70 | 98.5 |
|  | " | 2 | 4.13 | 15 | 87 | 25.1 | 100 |
| 14 | Silica[e] | 1 | 4.07 | 15 | 86 | 77.4 | 98.9 |
|  | " | 2 | 4.07 | 15 | 87 | 54.4 | 98.2 |
| 15 | Silylated Silica[f] | 1 | 4.07 | 15 | 87 | 98.0 | 100 |
|  | " | 2 | 4.07 | 16 | 85 | 56.1 | 100 |

[a]Reactions were run in a 600 mL Hastalloy C Parr reactor in cyclohexane under about 1000 psig $H_2$.
The metal loading is 2% iridium/0.5% ruthenium in all cases.
[b]Engelhard 3952E Alumina.
[c]Grace-Davison SMR 55-10384.
[d]Titanium(0.6%)-modified Davison 57 Silica.
[e]IST Isolute ® SI Silica.
[f]IST Isolute ® C2(EC) Silica.

What is claimed is:

1. A process for making 2,3-dihalopropanol comprising the step of reacting 2,3-dihalopropanal with a hydrogenating agent in the presence of a heterogeneous mixed transition metal catalyst under the conditions such that 2,3-dihalopropanol is formed, wherein the heterogeneous mixed transition metal catalyst comprises an iridium metal as a first transition metal and at least a second transition metal selected from the group consisting of ruthenium, iron, molybdenum, tungsten, rhenium, osmium, or vanadium; and wherein the atomic ratio of iridium metal to said second transition metal is from about 0.02 to about 15 such that iridium metal plus the second transition metal used as a mixed metal catalyst provides a sustained high catalytic activity and a high selectivity to the 2,3-dihalopropanol superior to the pure iridium metal used as a metal catalyst.

2. The process in claim 1 wherein the second transition metal is ruthenium.

3. The process of claim 2 wherein the atomic ratio of iridium metal to ruthenium metal is from about 0.15 to 8.

4. The process of claim 3 wherein the atomic ratio of iridium metal to ruthenium metal is from about 0.3 to 2.

5. The process of claim 1 wherein the catalyst is a heterogeneous catalyst which contains the iridium and second transition metal deposited upon a supporting material.

6. The process of claim 5 wherein the supporting material is selected from the group consisting of silica, silylated silica, carbon, alumina, titania, zirconia, magnesia and combinations thereof.

7. The process of claim 6 wherein the supporting material is a silylated silica.

8. The process of claim 1 wherein the catalyst includes a Group I or transition metal promoter ion.

9. The process of claim 8 wherein the promoter ion is selected from the group consisting of Li, Na, K, Cs, Fe, Mo, W, V, Mn, Os, Pt, Pd, Rh and mixtures thereof.

10. The process of claim 9 wherein the promoter ion is K.

11. The process of claim 1 wherein the catalyst further contains a coordination ligand.

12. The process as described in claim 1 wherein the hydrogenating agent is molecular hydrogen.

13. The process of claim 12 wherein the consumed amount of molecular hydrogen to dihalopropanal is at least about 0.75:1.

14. The process of claim 12 which is carried out with a hydrogen partial pressure of at least about 14 psia.

15. The process of claim 1 wherein the 2,3-dihalopropanal is selected from the group consisting of 2,3-dichloropropanal; 2,3-dibromopropanal; 2,3-dicholoro-2-methylpropanal 2,3-dibromo-2-methylpropanal; and mixtures thereof.

16. The process of claim 1 wherein the 2,3-dihalopropanal is unsubstituted 2,3-dichloropropanal and the 2,3-dihalopropanol formed is 2,3-dichloropropanol.

17. The process of claim 1 wherein the 2,3-dihalopropanal is unsubstituted 2,3-dibromopropanal and the 2,3-dihalopropanol formed is 2,3-dibromopropanol.

18. The process of claim 1 which is carried out at a temperature of about 0° C. to about 200° C.

19. The process of claim 1 wherein the reaction mixture further contains a solvent.

20. The process of claim 19 wherein the solvent is selected from the group consisting of water, carboxylic acids, phenolic compounds, aliphatic alcohols, aliphatic and aromatic hydrocarbons, carbonates, ethers, glymes, glycol ethers, halogenated hydrocarbons and mixtures thereof.

21. The process of claim 1 wherein the reaction mixture further contains an acid scavenger.

22. The process of claim 21 wherein the acid scavenger is selected from the group consisting of alkali metal carbonates; alkali metal bicarbonates; alkali metal carboxylates; ammonium and phosphonium carboxylates, bicarbonates, carbonates; epoxides and mixtures thereof.

23. The process of claim 22 wherein the acid scavenger is epichlorohydrin.

24. The process of claim 1 comprising the step of reacting 2,3-dihalopropanal with at least a stoichiometric quantity of molecular hydrogen in the presence of the mixed transition metal catalyst and a solvent.

25. A process to make epihalohydrin comprising the steps of:
 (a) reducing 2,3-dihalopropanal as described in claim 1 to form 2,3-dihalopropanol; and
 (b) contacting the 2,3-dihalopropanol with a base, whereby an epihalohydrin is formed.

26. A process to make epihalohydrin comprising the steps of:
 (a) halogenating acrolein to make 2,3-dihalopropanal;
 (b) reducing 2,3-dihalopropanal as described in claim 1 to form 2,3-dihalopropanol; and
 (c) contacting the 2,3-dihalopropanol with a base, whereby an epihalohydrin is formed.

27. A process to make epihalohydrin comprising the steps of:
 (a) reacting a hydrocarbon which contains 3 carbon atoms with an oxidizing agent to form acrolein;
 (b) reacting acrolein with a molecular halogen to form 2,3-dihalopropanal;
 (c) reducing 2,3-dihalopropanal to form 2,3-dihalopropanol as described in claim 1 to form 2,3-dihalopropanol; and
 (d) contacting the 2,3-dihalopropanol with a base, whereby an epihalohydrin is formed.

* * * * *